US005643549A

United States Patent [19]

Rhodes

[11] Patent Number: 5,643,549

[45] Date of Patent: *Jul. 1, 1997

[54] LEUKOSTIMULATORY AGENT FOR IN VIVO LEUKOCYTE TAGGING

[75] Inventor: Buck A. Rhodes, Albuquerque, N.M.

[73] Assignee: Rhomed Incorporated, Albuquerque, N.M.

[*] Notice: The term of this patent shall not extend beyond the expiration date of Pat. No. 5,227,892.

[21] Appl. No.: 179,984

[22] Filed: Jan. 11, 1994

Related U.S. Application Data

[63] Continuation-in-part of Ser. No. 840,076, Feb. 20, 1992, Pat. No. 5,277,892.

[51] Int. Cl.$^6$ .................. A61K 51/08; A61K 38/00; A61B 5/055

[52] U.S. Cl. .................. 424/1.69; 424/1.41; 424/1.49; 424/1.73; 424/9.34; 424/9.35; 424/85.1; 530/300; 530/351; 530/304

[58] Field of Search .................. 424/1.11, 1.69, 424/1.41, 1.65, 1.73, 1.49, 9.34, 9.35, 85.1; 530/300, 351, 304

[56] References Cited

U.S. PATENT DOCUMENTS

| | | | |
|---|---|---|---|
| 3,812,264 | 5/1974 | Nouel | 424/1 |
| 4,289,747 | 9/1981 | Chu | 424/1 |
| 4,421,735 | 12/1983 | Haber | 424/1.1 |
| 4,424,200 | 1/1984 | Crockford et al. | 424/1 |
| 4,427,646 | 1/1984 | Olexa et al. | 424/1.1 |
| 4,455,290 | 6/1984 | Olexa et al. | 424/1.1 |
| 4,479,930 | 10/1984 | Hnatowich | 424/1.1 |
| 4,485,101 | 11/1984 | Coy et al. | 424/177 |
| 4,550,086 | 10/1985 | Reinherz et al. | 436/506 |
| 4,622,420 | 11/1986 | Meares et al. | 562/443 |
| 4,634,586 | 1/1987 | Goodwin et al. | 424/1.1 |
| 4,668,503 | 5/1987 | Hnatowich | 424/1.1 |
| 4,670,545 | 6/1987 | Fritzberg et al. | 534/14 |
| 4,724,212 | 2/1988 | Epstein | 435/240.27 |
| 4,732,864 | 3/1988 | Tolman | 436/547 |
| 4,735,210 | 4/1988 | Goldenberg | 128/654 |
| 4,810,693 | 3/1989 | Pickart | 514/18 |
| 4,853,371 | 8/1989 | Coy et al. | 514/12 |
| 4,861,579 | 8/1989 | Meyer, Jr. et al. | 424/1.1 |
| 4,870,015 | 9/1989 | Hoffman | 435/172.3 |
| 4,871,717 | 10/1989 | Coy et al. | 514/11 |
| 4,877,868 | 10/1989 | Reno et al. | 530/390 |
| 4,904,642 | 2/1990 | Coy et al. | 514/11 |
| 4,917,878 | 4/1990 | Thakur | 424/1.1 |
| 4,925,648 | 5/1990 | Hansen et al. | 424/1.1 |
| 4,926,869 | 5/1990 | Rubin et al. | 128/654 |
| 4,986,979 | 1/1991 | Morgan, Jr. et al. | 424/1.1 |
| 5,002,869 | 3/1991 | Schlossman et al. | 435/7.24 |
| 5,011,676 | 4/1991 | Thakur | 424/1.1 |
| 5,011,916 | 4/1991 | Bonnyman et al. | 534/12 |
| 5,023,237 | 6/1991 | Pickart | 514/18 |
| 5,053,493 | 10/1991 | Pak et al. | 530/402 |
| 5,059,588 | 10/1991 | Pickart | 514/12 |
| 5,061,641 | 10/1991 | Shochat et al. | 436/545 |
| 5,078,985 | 1/1992 | Rhodes | 424/1.1 |
| 5,079,343 | 1/1992 | Anderson et al. | 530/387 |
| 5,089,604 | 2/1992 | Washino et al. | 530/395 |
| 5,102,990 | 4/1992 | Rhodes | 530/391.5 |
| 5,116,596 | 5/1992 | Bremer et al. | 424/1.1 |
| 5,120,642 | 6/1992 | Schlossman et al. | 435/7.24 |
| 5,128,119 | 7/1992 | Griffiths | 424/1.1 |
| 5,143,712 | 9/1992 | Brandley et al. | 424/1.1 |
| 5,200,178 | 4/1993 | Strauss et al. | 424/1.1 |
| 5,223,426 | 6/1993 | Skibbens et al. | 435/240.27 |
| 5,225,180 | 7/1993 | Dean et al. | 424/1.1 |
| 5,240,693 | 8/1993 | Born et al. | 424/4 |
| 5,317,091 | 5/1994 | Subramanian | 424/1.53 |
| 5,328,679 | 7/1994 | Hansen et al. | 424/1.49 |
| 5,371,184 | 12/1994 | Rajagopalan et al. | 530/324 |

FOREIGN PATENT DOCUMENTS

| | | | |
|---|---|---|---|
| 2016235 | 9/1990 | Canada | 167/47 |
| 0135160 | 3/1985 | European Pat. Off. | 49/2 |
| 0188256 | 7/1986 | European Pat. Off. | 153/23 |
| 0237150 | 9/1987 | European Pat. Off. . | |
| 0284071 | 9/1988 | European Pat. Off. . | |
| 0389180 | 9/1990 | European Pat. Off. | 7/6 |
| 0403225 | 12/1990 | European Pat. Off. . | |
| 2225579 | 6/1990 | United Kingdom . | |
| WO8501442 | 4/1985 | WIPO . | |
| WO92US3675 | 8/1985 | WIPO . | |
| WO88/07382 | 10/1988 | WIPO | 49/2 |
| WO89/00051 | 1/1989 | WIPO . | |
| WO89/04666 | 6/1989 | WIPO | 37/24 |
| WO89/10760 | 11/1989 | WIPO | 49/2 |
| WO90/13317 | 11/1990 | WIPO | 49/2 |
| WO90/15626 | 12/1990 | WIPO . | |
| WO90/15818 | 12/1990 | WIPO | 5/9 |
| WO91/00111 | 1/1991 | WIPO . | |
| WO91/01144 | 2/1991 | WIPO . | |
| WO91/17173 | 11/1991 | WIPO . | |

OTHER PUBLICATIONS

"Basic and Clinical Immunology", Seventh Edition, Stites and Terr, Chapter 5, p. 614, 1991, Publ. Appleton & Lange.

Albert, et al., Abstract "A Somatostatin Analogue to Image–SS–Receptor–Positive Tumors: . . ." *J. Nucl. Med.*, vol. 31 (1990).

Arnold, et al., "Engineered Metal–Binding Proteins: Purification to Protein Folding," *Science*, vol. 252, pp. 1796–1797 (Jun. 28, 1991).

Astaldi, et al., "Antibodies to Phytohaemagglutinin," *The Lancet*, pp. 502–553 (Aug. 27, 1966).

Bakker, et al., "In Vivo Use of a Radioiodinated Somatostatin Analog: Dynamics, Metabolism, and binding to Somatostatin Receptor–Positive Tumors in Man," *J. Nucl Med.*, vol. 32, No. 6, pp. 1184–1191 (1991).

(List continued on next page.)

*Primary Examiner*—Gary E. Hollinden
*Assistant Examiner*—Michael G. Hartley
*Attorney, Agent, or Firm*—Darby & Darby

[57] ABSTRACT

Methods and reagents for the in vivo tagging of leukocytes, and in particular lymphocytes, with a leukostimulatory agent and a linked medically useful metal ion, including a radioisotope, and subsequent detection of leukocyte or lymphocyte trafficking and sites of concentrated leukocytes or lymphocytes within the patient by radiodetection or paramagnetic means are disclosed.

12 Claims, No Drawings

OTHER PUBLICATIONS

Baker, et al., "Receptor Scintigraphy with a Radioiodinated Somatostatin Analog: Radiolabeling, Purification, Biologic Activity, and In Vivo Application in Animals," *J. Nucl. Med.*, vol. 31, No. 9, pp. 1501–1509 (Sep. 1990).

Baidoo, et al., "$^{99m}$Tc Labeling of Proteins: Initial Evaluation of a Novel Diaminedithiol Bifunctional Chelating Agent," *Cancer Res. Supp)*, vol. 50, pp. 799–803 (Apr. 1984).

Bryson, et al., "Neutral Technetium(V) Complexes with Amide–Thiol–Thioether Chelating Ligands," *Inorg. Chem.*, vol. 27, pp. 2154–2161 (1988).

Bryson, et al., "Protecting Groups in the Preparation of Thiolate Complexes of Technetium," *Inorg. Chem.*, vol. 29, pp. 2948–2951 (1990).

Byrd, "Inhibition of the Mitogenic Factor in Phytohaemagglutinin by an Antiserum," *Nature*, pp. 622–624 (Feb. 1967).

Byrne, et al., "Technetium–99m Bifunctional Chelating Agent–Thiolactone for Coupling to Biomolecules, $N_2N_2$ Ligand for Chelation to Technetium," *J. Nucl. Med.*, vol. 24, p. 126 (1983).

Castronovo, et al., "Laminin Receptor Complementary DNA–deduced Synthetic Peptide Inhibits Cancer Cell Attachment to Endothelium," *Cancer Res.*, vol. 51, pp. 5672–5678 (Oct. 1991).

Cioce, et al., "Increased Expression of the Laminin Receptor in Human Colon Cancer," *Articles*, J. of National Cancer Insti., vol. 83, No. 1, pp. 29–36 (Jan. 1991).

Cox, "Technetium Labeled Somatostatis a Potential Agent for In Vivo Tumor Localization," *7th Int'l Symp. on Radiopharm.*, p. 16 (1991) Abstract.

Davison, "A New Class of Oxotechnetium (5+) Chelate Complexes Containing a $TcON_2S_2$ Core," *Amer. Chem Soc.*, vol. 20, No. 6, pp. 1629–1632 (1981).

Drapeau, "Synthetic C5a Receptor Agonists," *Biochem. Pharm.*, vol. 45, No. 6, pp. 1289–1299 (1993).

El–Hag, et al., "Immunosuppression by Activated Human Neutrophils," *J. Immun.*, vol. 139, No. 7, pp. 2406–2413 (Oct. 1987).

Fischman, et al., "Imaging Focal Sites of Bacterial Infection in Rats with Indium–111–Labeled Chemotactic Peptide Analogs," *J. Nucl. Med.*, vol. 32, No. 3, pp. 483–491 (Mar. 1991).

Fritzberg, et al., "Approaches to Radiolabeling of Antibodies for Diagnosis and Therapy of Cancer," *Pharm. Res.*, vol. 5, No. 6, pp. 325–334 (1988).

Fritzberg, et al., "Synthesis and Biological Evaluation of Tc–99m N,N'–Bis(mercaptoacetyl)–2,3–diaminopropanoate: A Potential Replacement for [$^{131}$]θ–iodohippurate," *J. Nucl. Med.*, vol. 23, No. 7, pp. 592–598 (1982).

Ghadiri, et al., "Peptide Architecture. Design of Stable α–Helical Metallopeptides via a Novel Exchange–Inert $RU^{III}$ Complex," *J. Am. Chem. Soc.*, vol. 112 pp. 9633–9635 (1990).

Granowska, et al., "A Tc–99m Labelled Monoclonal Antibody,PR1A3, for Radioimmunoschintigraphy, RIS, of Colorectal Cancer," *J. Nucl. Med.*, vol. 30, p. 748 (No. 80) (1989).

Greaves, et al., "Lymphocyte Activation—Binding Sites for Phytomitogens on Lyphycyte Subpopulations," *Clin. Exp. Immunol.*, vol. 10, pp. 537–554 (1972).

Hnatowich, et al., "Antibody Radiolabeling, Problems and Promises," *Nucl. Med. Biol.*, vol. 17, No. 1 pp. 49–55 (1990).

Hnatowich, et al., "Recent Developments in the Radiolabeling of Antibodies with Iodine, Indium, and Technetium," *Sem. in Nucl. Med.*, vol. XX, No. 1, pp. 80–91 (Jan. 1990).

Hoffman, et al., "Synthesis of Mitogenic Phytohemagglutinin–L in *Escherichia coli*,"*Bio/Tech.*, vol. 5, pp. 157–160 (Feb. 1987).

Houston, et al., "Specific In Vivo Localization of Monoclonal Antibodies Directed Against the Thy 1.1 Antigen," *J. Immun.*, vol. 125, No. 2, pp. 837–843 (1980).

Hynes "Integrins: A Family of Cell Surface Receptors," *Review*, Cell, vol. 48, pp. 549–554 (1987).

Iverson, et al., "Metalloantibodies," *Reports*, Science, vol. 249, pp. 659–662 (Aug. 1990).

Janeczek, et al., "Autoradiographic Analysis of Formylpeptide Chemoattractant Binding, Uptake and Intracellular Processing of Neutrophils," *J. Cell Sci* 94, pp. 155–168 (1989).

Jaziri, et al., "Specific Binding Sites on Human Phagocytic Blood Cells for Gly–Leu–Phe and Val–Glu–Pro–Ile–Pro–Tyr, Immunostimulating Peptides from Human Milk Proteins," *BioChimica et Biophysica Acta*, vol. 1160, pp. 251–261 (1992).

Khaw, et al., "Technetium–99m Labeling of Antibodies to Cardiac Myosin Fab and to Human Fibrinogen," *J. Nucl. Med*, vol. 23, No. 11, pp. 1011–1019 (1982).

Krejcarek, et al., "Covalent Attachment of Chelating Groups to Macromolecules," *Biochm. and Biophys. Res. Comm.*, vol. 77, No. 2, pp. 581–585 (1977).

Kwekkeboom, et al., "Octrolotide Scintigraphy in Neuro–Endocrine Tumors," *J. Nucl. Med*, vol. 32, No. 5, p. 981 (May 1991) Abstract.

Kwekkeboom, et al., "Radioiodinated Somatostatin Analog Schintigrahy in Small–Cell Lung Cancer," *J. Nucl. Med.*, vol. 32, No. 10, pp. 1845–1848 (Oct. 1991).

Lavender, et al., "Kinetics of Indium–III Labelled Lymphocytes in Normal Subjects and Patients with Hodgkin's Disease," *British Med. Jour.*, vol. 2, pp. 797–799 (Sep. 1977).

Lever, et al., "Synthesis of a Novel Bifunctional Chelate Designed for Labeling Proteins with Technetium–99m," *Tetrahedron Letters*, vol. 29, No. 26 pp. 3219–3222 (1988).

Lindahl–Kiessling, "Mechanism of Phytohemagglutinin (PHA) Action," *Exp. Cell Res.*, vol. 70, pp. 17–26 (1972).

Loutfi, et al., "In Vivo Imaging of Rat Lymphocytes with an Indium 111–Labelled Anti–T Cell Monoclonal Antibody: a Comparison with Indium 111–Labelled Lymphocytes," *Eur. J. Nucl. Med.*, vol. 16, pp. 69–76 (1990).

Moser, et al., "Neutrophil–Activating Peptide 2 and gro/Melanoma Growth–Stimulatory Activity Interact with Neutrophil–Activating Peptide 1/Interleukin 8 Receptors on Human Neutrophils," *J. Biol. Chem*, vol. 266, No. 16 (pp. 10666–10671) (Jun. 1991).

Paik, et al., "The Labeling of High Affinity Sites of Antibodies with $^{99m}$Tc," *Int. J. Nucl. Med. Biol.*, vol. 12, No. 1, pp. 3–8 (1985).

Pak, et al., "A Rapid and Efficient Method for Labeling IgG Antibodies with Tc–99m and Comparison to Tc–99m Fab' Antibody Fragments," *J. Nucl. Med.*, vol. 30, No. 5, p. 793 (No. 268) (1989) Abstract.

Pettit, et al., "Iodination and Acceptance Testing of Antibodies," *Masson Publ. USA Inc, NY*, pp. 99–109 (1987).

Rhodes, "Considerations in the Radiolabeling of Albumin," *Sem. Nucl. Med.*, vol. 4, No. 3, pp. 281–293 (1974).

Rhodes, et al., "Technetium–99m Labeling of Murine Monoclonal Antibody Fragments," *J. Nucl. Med.*, vol. 27, No. 5, pp. 685–693 (1986).

Rhodes, et al., "Quality Control Test for Immunoreactivity of Radiolabeled Antibody," *BioTech.*, vol. 8, No. 1, pp. 70–74 (1990).

Rhodes, "Direct Labeling of Proteins with $^{99m}$Tc," *Nucl. Med. Biol.*, vol. 18, No. 7 pp. 667–676 (1991).

Rosenberg, "Lymphokine–Activated Killer Cells: A New Approach to Immunotherapy of Cancer," *JNCI*, vol. 75, No. 4, pp. 595–603 (Oct. 1985).

Schumacher, et al., "High– and Low–Affinity Binding of Gro$\alpha$ and Neutrophil–Activating Peptide 2 to Interleukin 8 Receptors on Human Neutrophils," *Proc. Nat'l Acad. Sci. USA*, vol. 89, pp. 10542–10546 (Nov. 1992).

Seaman, et al., "Selective Manipulation of the Immune Response in Vivo by Monoclonal Antibodies," *Ann. Rev. Med.*, vol. 39, pp. 231–241 (1988).

Seifert, et al., "Technetium–99 and 99m Chelates with N–Donor Ligands: A New Class of Potential Cationic Radiopharmaceuticals," *Technetium in Chem. and Nucl. Med.*, pp. 19–23 (1983).

Sharon, et al., "Carbohydrates in Cell Recognition," *Sci. Amer.*, pp. 82–89 (Jan. 1993).

Sonnenberg, et al., "Isolation of $\alpha 6\beta 1$ Integrins from Platelets and Adherent Cells by Chromatography on Mouse Laminin Fragment E8 and Human laminin Pepsin Fragment," *Exp. Cell Res.*, vol. 197, pp. 234–244 (1991).

Tandon, et al., "Interaction of Human Platelets with Laminin and Identification of the 67 kDa Laminin Receptor on Platelets," *Biochem. J.*, vol. 274, pp. 535–542 (1991).

Thakur, et al., "Indium–111–Labeled Autologous Leukocytes in Man," *J. Nucl. Med.*, vol. 18, No. 10, pp. 1014–1021 (1977).

Thakur, et al., "Indium–111–Labeled Leukocytes for the Localization of Abscesses: Preparation, Analysis, Tissue Distribution, and Comparison with Gallium–67 Citrate in Dogs," *J. Lab. Clin. Med.*, vol. 89, pp. 217–228 (Jan. 1977).

Thakur, "A Look at Radiolabeled Blood Cells," *Nucl. Med. Biol.*, vol. 13, No. 2, pp. 147–158 (1986).

Thompson, et al., "Identification of an Amino Acid Sequence in the Laminin A Chain Mediating Mast Cell Attachment and Spreading," *Immun.*, vol. 72, pp. 144–149 (1991).

Tubis, et al., "The Preparation of $^{99m}$Technetium–Labeled Cystine, Methionine and a Synthetic Polypeptide and Their Distribution in Mice," *Int'l J. Ap. Rad. and Isotropes*, vol. 19, pp. 835–840 (1968).

Valle, et al., "Zinc Coordination, Function, and Structure of Zinc Enzymes and Other Proteins," *Biochem.*, vol. 29, No. 24, pp. 5647–5659 (Jun. 1990).

VanEpps, et al., "Fucose–Binding Lotus Tetragonolobus Lectin Binds to Human Polymorphonuclear Leukocytes and Induces a Chemotactic Response," *J. Immun.*, vol. 119, No. 3, pp. 1187–1189 (1977).

Wagstaff, et al., "Human Lymphocyte Traffic Assessed by Indium–111 Oxine Labelling: Clinical Observations," *Clin. Exp. Immunol.*, vol. 43, pp. 443–449 (1981).

Walz, et al., "A Novel Cleavage Product of $\beta$–Thromboglobulin Formed in Cultures of Stimulated Mononuclear Cells Activates Human Neutrophils," *Biochem. and Biophys. Res. Comm.*, vol. 159, No. 3, pp. 969–975 (1989).

Weber, "Kinetics of the reaction of Kidney–Bean Leucoagglutinion with Human Lymphocytes," *Experimantia*, vol. 29, pp. 863–865 (1973).

Wensel, et al., "Bifunctional Chelating Agents for Binding Metal Ions to Proteins," *Radioimmunoimaging and Radioimmunotherapy*, pp. 185–196 (1983).

Wimer, "Potential Therapeutic Applications of PHA–L4 The Mitogenic Isolectin of Phytohemagglutinin," *Mol. Biother.*, pp. 1–8 (1990).

Wimer, "Therapeutic Activities of PHA–L4, the Mitogenic Isolectin of Phytohemagglutinin", *Mol. Biother.*, vol. 2, pp. 74–90 (1990).

Wimer, "Characteristics of PHA–L4, The Mitogenic Isolectin of Phytohemagglutinin, as an Ideal Biologic Response Modifier", *Mol. Biother.*, vol. 2, pp. 4–17 (1990).

Wimer, "The Ideal Biological Response Modifier," *Mol. Biother.*, vol. 1, No. 6, pp. 311–317 (1989).

Fischman, Alan J., et al., "A Ticket to Ride: Peptide Radiopharmaceuticals," *Journal of Nucl. Med.*, vol. 34, No. 12, pp. 2253–2263 (Dec. 1993).

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: Peptide ( i i i ) HYPOTHETICAL: No ( i v ) ANTI-SENSE: No ( x i ) SEQUENCE DESCRIPTION: SEQ ID NO: 1:

```
Ala  Glu  Leu  Arg  Cys  Met  Cys  Ile  Lys  Thr  Thr  Ser  Gly  Ile
1                   5                        10
His  Pro  Lys  Asn  Ile  Gln
15                  20
```

( 2 ) INFORMATION FOR SEQ ID NO:2:

( i ) SEQUENCE CHARACTERISTICS:
        ( A ) LENGTH: 3 amino acids
        ( B ) TYPE: amino acid
        ( C ) STRANDEDNESS: single
        ( D ) TOPOLOGY: linear ( i i ) MOLECULE TYPE: Peptide ( i i i ) HYPOTHETICAL: No ( i v ) ANTI-SENSE: No ( x i ) SEQUENCE DESCRIPTION: SEQ ID NO: 2:

```
Gly  Leu  Phe
1
```

( 2 ) INFORMATION FOR SEQ ID NO:3:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: Peptide ( i i i ) HYPOTHETICAL: No

```
(iv) ANTI-SENSE: No (xi) SEQUENCE DESCRIPTION: SEQ ID NO: 3:

Val  Glu  Pro  Ile  Pro  Tyr
    1                 5
```

LEUKOSTIMULATORY AGENT FOR IN VIVO LEUKOCYTE TAGGING

CROSS-REFERENCE TO RELATED APPLICATIONS

This application is a continuation-in-part application of Ser. No. 07/840,076 filed on Feb. 20, 1992 now U.S. Pat. No. 5,277,892, issued Jan. 11, 1994, entitled In Vivo Lymphocyte Tagging; and is related to U.S. Pat. No. 5,102,990, entitled Direct Radiolabeling of Antibodies and Other Proteins with Technetium or Rhenium; U.S. Pat. No. 5,078,985, entitled Radiolabeling Antibodies and Other Proteins with Technetium or Rhenium by Regulated Reduction; U.S. Pat. No. 5,346,687, entitled Direct Radiolabeling of Antibody Against Stage Specific Embryonic Antigen for Diagnostic Imaging; and U.S. Pat. No. 5,460,785, entitled Direct Labeling of Antibodies and Other Proteins with Metal Ions; and, U.S. Pat. No. 5,443,816, entitled Peptide-Metal Ion Pharmaceutical Preparation and Method; the teachings of all of the foregoing are incorporated herein by reference.

LICENSE RIGHTS

The U.S. Government has a paid-up license in this invention and the right in limited circumstances to require the patent owner to license others on reasonable terms as provided for by the terms of Small Business Innovative Research Grant No. 1 R43 AR41124 awarded by the National Institute of Arthritis and Musculoskeletal and Skin Diseases, Department of Health and Human Services.

BACKGROUND OF THE INVENTION

1. Field of the Invention (Technical Field)

The present invention relates to the in vivo tagging of leukocytes, and in particular lymphocytes, with radioactive tracers and other diagnostically useful metal ions, and subsequent detection of lymphocyte trafficking and sites of concentrated lymphocytes within the mammal by radiodetection or other means.

2. Description of the Related Art, Including Information Disclosed under 37 C.F.R. Sections 1.97–1.99 (Background Art)

This application covers generally the development of a pan-T-lymphocyte tracer that can be used both to study trafficking of stimulated lymphocytes and as a diagnostic radiopharmaceutical or magnetic resonance imaging diagnostic pharmaceutical, for use in chronic infections such as osteomyelitis and granulomatous diseases and for other conditions. One of the disadvantages of using only monoclonal antibody tracers to tag circulating lymphocytes is that they are generally species specific, and a monoclonal antibody that recognizes a specific subset of human lymphocytes can be used only for studies in humans. Thus, there is a need for specific tracers that can be used in both laboratory animals and man, so that experimental studies, the results of which will be extrapolated to humans, can be conducted.

One class of pan-T-lymphocyte tracers disclosed herein are leukostimulatory lectins, and particularly the plant-derived lectin, phytohemagglutinin-L4 (PHA-L4). This isolectin binds the CD3 receptor on T-lymphocytes of both laboratory animals and humans. Wimer, B. M., "The ideal biological response modifier," *Mol Biother* 1:311–317, 1989. It also stimulates the lymphocytes to differentiate and divide (Wimer, B. M., "Characteristics of PHA-L4, the mitogenic isolectin of phytohemagglutinin, as an ideal biologic response modifier," *Mol Biother* 2:4–17, 1990); thus, the labeled molecule provides a tracer that can be used to track stimulated lymphocytes.

Although the use of PHA as a drug has been studied for many years (See generally, Wimer, B. M., "Therapeutic activities of PHA-L4, the mitogenic isolectin of phytohemagglutinin," *Mol Biother* 2:74–90, 1990; and, Wimer, B. M., "Potential therapeutic applications of PHA-L4, the mitogenic isolectin of phytohemagglutinin," *Mol Biother* 2:196–200, 1990), it has not found a permanent place in the routine practice of medicine.

Native PHA consists of four subunits and has both leuko- and erythro-agglutinating properties, as well as leukostimulatory properties. The L4 isolectin of PHA carries only the leukoagglutinating and stimulating species, and has been found to bind the CD3 receptor on T-lymphocytes. Greaves, M. F., Bauminger, S., Janossy, G., "Lymphocyte activation. III. Binding sites for phytomitogens on lymphocyte subpopulations," *Clin Exp Immunol* 10:537–554, 1972.

PHA was originally isolated as an aqueous extract of the beans of the genus Phaseolus, especially the red kidney bean, *Phaseolus vulgaris*. At least two active ingredients have been identified in the extract, a mucoprotein and a glycoprotein. The L-4 isolectin appears to be one of five isolectins that comprise the PHA glycoprotein. PHA may be prepared by a number of means, and is commercially available from E-Y Laboratories in a variety of forms, including the glycoprotein tetramer and the purified L-4 isolectin of PHA.

PHA-L4 may also be prepared using recombinant DNA technology. Hoffman and Donaldson have reported the methodology for synthesis of non-erythroagglutinating PHA-L4 in *Escherichia coli*. Hoffman, L. M., and Donaldson, D. D., "Synthesis of mitogenic phytohemagglutinin-L in *Escherichia coli*," *Biotechnology* 5:157–160, 1987; Hoffman, L. M., U.S. Pat. No. 4,870,015, Method and Composition for Producing Lectin in Microorganisms.

One advantage of using labeled PHA-L4 or other lectin-based leukostimulatory agents in place of monoclonal antibody tracers is the possibility of using the leukostimulatory agent, such as PHA-L4 isolectin, in several species. Generally speaking, monoclonal antibodies against the human CD3 receptor do not bind to murine CD3 receptors, and this lack of a lymphocyte tracer applicable to the laboratory mouse has limited many basic studies of adoptive immunotherapy.

Rosenberg (Rosenberg, S., "Lymphokine-activated killer cells: A new approach to immunotherapy of cancer," *JNCI* 75:595–603, 1985) notes that immunologically active cells tend to be larger than normal resting cells. They are also different in other aspects, such as their level of oxidative metabolism, degranulation, and adherence. el-Hag, A., Clark, R. A., "Immunosuppression by activated human neutrophils. Dependence on the myeloperoxidase system," *J Immunol* 139:2406–2413, 1987. Thus, it appears that cells that are stimulated and labeled with radiolabeled PHA-L4 will traffic differently than the general population of lymphocytes, which can be labeled by methods such as $^{111}$In oxine. Thakur, M. L., Coleman, R. E., Welch, M. J., "Indium-111-labeled leukocytes for the localization of abscesses: preparation, analysis, tissue distribution, and comparison with gallium-67 citrate in dogs," *J Lab Clin Med* 89:217–228, 1977; and, Thakur, M. L., Lavender, J. P., Arnot, R. N., et al, "Indium-111-labeled autologous leukocytes in man," *J Nucl Med* 18:1014–1021, 1977.

In vivo imaging with $^{111}$In-labeled lymphocytes in a study of patients with Hodgkin's disease was demonstrated by Lavender et al in 1977. Lavender, J. P., Goldman, J. M., Arnot, R. N., Thakur, M. L., "Kinetics of indium-111 labeled lymphocytes in normal subjects and patients with Hodgkin's disease," *Brit Med J* 2:797–799, 1977. Such studies have been limited by the extreme radiosensitivity of lymphocytes labeled internally with $^{111}$In. A more recent approach has been to use radiolabeled antibodies that bind to cell surface antigens to label the cells in such a way that the radionuclide is distanced from the cell nucleus. Thakur, M. L., U.S. Pat. No. 4,917,878, Novel Use of a Radiolabelled Antibody Against Stage Specific Embryonic Antigen for the Detection of Occult Abscesses in Mammals; Houston, L. L., Nowinski, R. C., Bernstein, I. D., "Specific in vivo localization of monoclonal antibodies directed against the Thy 1.1 antigen," *J Immunol* 125:837–843, 1980; and, Loutfi, I., Chisholm, P. M., Bevan, D., Lavender, J. P. "In vivo imaging of rat lymphocytes with an indium 111-labeled anti-T cell monoclonal antibody: a comparison with indium-111-labeled lymphocytes," *Eur J Nucl Med* 16:69–76, 1990.

Labeled lymphocytes are useful for studying lymphocyte trafficking and for diagnostic imaging of chronic infections and granulomas, and some tumors. Wagstaff, J., Gibson, C., Thatcher, N., et al, "A method for following human lymphocyte traffic using Indium-111 oxine labeling," *Clin Exp Immunol* 43:443–449, 1981; and, Thakur, M. L., "A look at radiolabeled blood cells," *Nucl Med Biol* 13:147–158, 1986.

The use of antibodies for in vivo tagging of leukocytes is known in the art. Goodwin, D. A., and Meares, C. F., U.S. Pat. No. 4,634,586, Reagent and Method for Radioimaging Leukocytes, teach a method in which leukocytes are radioimmunoimaged by injecting patients with an immunoreactive nonleukocidal conjugate of an anti-leukocyte and a gamma-emitting radioactive metal chelate, waiting for the conjugate to localize on the leukocytes, injecting the patient with an antibody to the conjugate to clear the blood of background nonlocalized conjugate and visualizing the leukocytes by scintillation scanning. The method can also be used without the step of injecting the second antibody to clear background nonlocalized antibody. Thakur, M. L., U.S. Pat. No. 4,917,878, Novel Use of a Radiolabelled Antibody Against Stage Specific Embryonic Antigen for the Detection of Occult Abscesses in Mammals, teaches a method whereby antibodies against a particular antigen found on human granulocytes, stage specific embryonic antigen-1, are radiolabeled using a bifunctional chelating agent, and the resulting radiolabeled antibody reagent injected under conditions which allow the reagent to accumulate at sites of occult abscess.

The use of radioisotopes to label biologically derived substances is well known. These compositions can be used in assays, can be administered to the human body to visualize or monitor functioning of various parts of the body, and can be used for therapy. A variety of radioisotopes, including isotopes of iodine, technetium, indium, gallium, yttrium and rhenium have been used.

Different methods can be used to radiolabel biological substances with radioisotopes. For iodine, a variety of iodination methods, such as chloramine-T, iodine monochloride, enzymatic iodination, electrolytic procedures and conjugation labeling, are well recognized. (Pettit, W.A., et al, "Iodination and acceptance testing of antibodies," *Tumor Imaging: The Radioimmunochemical Detection of Cancer*, S. W. Burchiel and B. A. Rhodes, Eds., Masson Publishing USA Inc., New York, 1982, pp 99– 109.) Bifunctional chelate methods, such as DTPA conjugation, can be used to label antibodies with $^{99m}$Tc, $^{111}$In, $^{67}$Ga, $^{68}$Ga or similar radionuclides. (Wensel, T. G. and Meares, C. F., "'Bifunctional' Chelating Agents for Binding Metal Ions to Proteins," *Radioimmunoimaging and Radioimmunotherapy*, S W Burchiel and B A Rhodes, eds., Elsevier Publishing Co., New York, 1983, pp 185–196.) The bifunctional chelate method was introduced by Krejcarek, G. E. and Tucker, K. L. (*Biophys Res Comm* 77:581–585, 1977) and has been widely employed in many variations using a broad variety of bifunctional chelating agents.

U.S. Pat. No. 4,479,930 to Hnatowich, D. J., discloses methods of radiolabeling using a dicyclic dianhydride of compounds such as ethylenediaminetetraacetic acid or diethylenetriaminepentaacetic acid. The patent also discloses chemical compositions containing the chelating agents and proteins or polypeptides. U.S. Pat. No. 4,668,503 to Hnatowich, D. J., discloses a process for labeling amines with $^{99m}$mTc in the presence of a stannous reducing agent. U.S. Pat. No. 4,622,420 to Meares, C. F., et al, discloses chelating agents which are analogs of ethylenediaminetetraacetic acid, ethylenediaminatriacetic acid or ethylenediaminepentaacetic acid which are useful in attaching radiolabels to biological molecules. Numerous other methods of labeling proteins and like substances which include lysine-containing amino acid groups, including those disclosed by Haber, E., and Khaw, B. A., U.S. Pat. No. 4,421,735; and by Fritzberg, A. R., and Kasina, S., U.S. Pat. No. 4,670,545, and by Baidoo, K. E., et al, "$^{99m}$Tc Labeling of Proteins: Initial Evaluation of Novel Diaminedithiol Bifunctional Chelating Agent," *Cancer Res (Supp)* 50:799s–803s, 1990, are well known in the art. A review article by Fritzberg et al discusses the general bifunctional chelate methods which may be used (Fritzberg, A. R., Berninger, R. W., Hadley, S. W., and Wester, D. W., "Approaches to radiolabeling of antibodies for diagnosis and therapy of cancer," *Pharm Res* 5:325–334, 1988).

Another general approach is direct labeling, which works with antibodies and other proteins containing accessible disulfide bonds or monosulfides. Although several direct methods have been reported, the first direct method capable of providing a sufficiently strong bond between the protein and the $^{99m}$Tc for in vivo applications was the direct or pretinning method described in U.S. Pat. No. 4,424,200, entitled Method for Radiolabeling Proteins with Technetium-99m, to Crockford, D. R., and Rhodes, B. A. In this method, a single reduction compound, consisting of stannous [Sn(II)] chloride and other salts which serves both to reduce the protein, thereby exposing the disulfide bonds, and to reduce the sodium pertechnetate, is used. With this method, many proteins can be successfully radiolabeled with $^{99m}$Tc. In U.S. Pat. No. 5,078,985, entitled Radiolabeling Antibodies and Other Proteins with Technetium or Rhenium by Regulated Reduction, to Rhodes, B. A., a method is provided in which any of a variety of reducing agents can be used to reduce disulfide bonds, the reducing agent is then removed, a source of Sn(II) added, and the preparation then labeled.

Other methods for direct labeling have been reported on (Schwarz, A., and Steinstruaber, A., "A novel approach to Tc-99m-labeled monoclonal antibodies," *J Nucl Med* 28:721, 1987; Pak, K. Y., et al, "A rapid and efficient method for labeling IgG antibodies with Tc-99m and comparison to Tc-99m Fab'". *J Nucl Med* 30:793, 1989; Granowska, M., et al, "A Tc-99m-labeled monoclonal antibody, PR1A3, for radioimmunoscintigraphy," *J Nucl Med* 30:748, 1989; Reno, J. W., U.S. Pat. No. 4,877,868, Radionuclide Antibody Coupling). In the equivalent methods disulfide reducing agents other than stannous salts were used. Pak et al used dithiothreitol to reduce the disulfide bonds of the antibody;

Swartz and Steinsbruaber, and Granowska et al used 2-mercaptoethanol; Reno used dithiothreitol (DTT) to reduce the disulfide groups of the protein, then protected the reactive sulfides with Zn (II) or other sulfhydryl group derivatizing reagents. Also some of these investigators (Swartz and Steinsbruaber, and Granowska et al) reduced the $^{99m}$Tc prior to adding it to the reduced antibody. The review by Rhodes (Rhodes, B. A., "Direct Labeling of Proteins with $^{99m}$Tc," Nucl Med Biol 18:667–676, 1991) covers direct labeling methods in detail, while the reviews of Hnatowich generally cover radiolabeling methods (Hnatowich, D. J., "Antibody radiolabeling, problems and promises," Nucl Med Biol 17:49–55 (1990); and, Hnatowich, D. J., "Recent developments in the radiolabeling of antibodies with iodine, indium, and technetium," Semin Nucl Med 20:80–91, 1991).

SUMMARY OF THE INVENTION
(DISCLOSURE OF THE INVENTION)

In accordance with the present invention, a method is provided for detecting concentrations of leukocytes in a mammalian patient, in which the patient is administered an effective amount of a reagent comprising a leukostimulatory agent and a linked medically useful metal ion under conditions which allow the reagent to bind to leukocytes, and concentrations of leukocytes by are detected by metal ion detection means. This method may be employed to locate sites of concentration of leukocytes which are associated with abscesses, inflammations, lesions or tumors.

In one embodiment, the leukostimulatory agent is a lectin. Lectins which can be used include phytohemagglutinin, concanavalin A and pokeweed mitogen. In the case of phytohemagglutinin, the L4 isolectin of phytohemagglutinin may be used. It is also possible to use leukostimulatory agents which are antibody, which may be in the form of either monoclonal antibodies or monoclonal antibody fragments.

A variety of types of leukocytes may be detected; one class of leukocytes useful in practicing this invention are lymphocytes, and particularly T lymphocytes. The leukostimulatory agent may bind to a CD3 receptor found on T lymphocytes.

A variety of imaging methods may be used to detect concentrations of leukocytes by metal ion detection means. These include gamma scintigraphy, specific photon emission computerized tomography, positron emission tomography and magnetic resonance imaging. Similarly, a variety of medically useful metal ions may be used; these include indium, technetium, gallium, ruthenium, iodine, yttrium, lead and copper.

The leukostimulatory agent can include a chelating agent, which may be a bifunctional chelating agent. Representative bifunctional chelating agents include cyclic anhydride of diethylenetriaminepentaacetic acid and diaminedithiol. It is also possible to employ a bifunctional chelating agent which contains one or more disulfide bonds. In the event that a bifunctional chelating agent with one or more disulfide bonds is used, it can be labeled by incubating the leukostimulatory agent containing disulfide bonds with a first reducing agent, the period of incubation being sufficient to reduce available disulfide bonds to thiolate groups while preventing excessive fragmentation of the protein; substantially removing the first reducing agent from the thiolate-containing leukostimulatory agent; adding a source of Sn (II) agent to the thiolate-containing leukostimulatory agent in a sufficient amount to form Sn (II)-containing and sulfur-containing complexes; and labeling the Sn (II)-containing and sulfur-containing complexes by adding the medically useful metal ion, whereby the metal ion displaces the Sn (II) agent and the metal ion and thiolate-containing protein form metal ion-containing and sulfur-containing complexes.

In the event that a leukostimulatory agent which contains disulfide bonds is used, such as an antibody, or a specific monoclonal antibody or monoclonal antibody fragments, a different method may be used for detecting concentrations of leukocytes in a patient. In this method, the leukostimulatory agent containing disulfide bonds is incubated with a first reducing agent, the period of incubation being sufficient to reduce available disulfide bonds to thiolate groups while preventing excessive fragmentation of the leukostimulatory agent; the first reducing agent is substantially removed from the thiolate-containing leukostimulatory agent; a source of Sn (II) agent is added to the thiolate-containing leukostimulatory agent in a sufficient amount to form Sn (II)-containing and sulfur-containing complexes; the Sn (II)-containing and sulfur-containing complexes is labeled by adding a medically useful metal ion, whereby the medically useful metal ion displaces the Sn (II) agent and the metal ion and thiolate-containing leukostimulatory agent form metal ion-containing and sulfur-containing complexes; the patient is administered an effective amount of the metal ion-containing and sulfur-containing leukostimulatory agent under conditions which allow the metal ion-containing and sulfur-containing leukostimulatory agent to bind to leukocytes; and concentrations of leukocytes are detected by metal ion detection means. The metal ion detection means used for imaging may include gamma scintigraphy, specific photon emission computerized tomography, positron emission tomography and magnetic resonance imaging. The medically useful metal ion may include isotopes of indium, technetium, gallium, ruthenium, iodine, yttrium, lead and copper. This preparation may also be used to determine concentrations of leukocytes which are associated with abscesses, inflammations, lesions or tumors.

The invention also discloses a method of performing a diagnostic procedure in a patient, in which a patient is administered a medically useful metal ion-labeled peptide in an amount effective for imaging, with the peptide including a leukostimulatory domain and a metal ion-binding domain, followed by imaging by metal ion detection means. The peptide with a leukostimulatory domain and a metal ion-binding domain can be selected from the group consisting of $(R_1)$—$[Y_1]_n$—$(R_2)$, $(R_1)$—$[Y_1$—$(R_2)$—$Y_1]_n$—$(R_3)$ and $(R_1)$—$[Y_1$—$(R_2)$—$Y_2]_n$—$(R_3)$ wherein, the medically useful metal ion-binding domain is selected from one of the group consisting of $[Y_1]_n$, $[Y_1$-$(R_2)$-$Y_1]_n$ and $[Y_1$-$(R_2)$-$Y_2]_n$ in which n is a number between 1 and about 6 and $Y_1$ and $Y_2$ are amino acids comprising a sulfur, nitrogen or oxygen which is available for binding to metal ions, or can be made available for binding to metal ions;

the leukostimulatory domain comprises at least one of the group consisting of $R_1$, $R_2$ and $R_3$ and further comprises an amino acid sequence containing from 1 to about 20 amino acids; and those portions of $R_1$, $R_2$ and $R_3$ not comprising the leukostimulatory domain each comprise an amino acid sequence containing from 0 to about 20 amino acids.

The leukostimulatory domain may be located in any one or more of $R_1$, $R_2$ or $R_3$, including situations in which the biological-function domain comprises all or part of two or more of $R_1$, $R_2$ or $R_3$. It is not required that the leukostimulatory domain constitute all of the amino acid sequence of any one of $R_1$, $R_2$ or $R_3$; that is, it is possible and contemplated that the leukostimulatory domain will be an amino acid sequence constituting a portion of the total amino acid sequence of any one of $R_1$, $R_2$ or $R_3$, with the remainder of that region being an amino acid sequence which is not the leukostimulatory domain.

The medically useful metal ion-binding domain of the peptide used in this method includes amino acid sequences containing cysteine, cystine, histidine, penicillamine, deacylated methionine, lysine, arginine, aspartic acid, glutamic acid or tyrosine. Specific medically useful metal ion-binding domains include the following:

[Cys]$_n$,

[Cys—(R$_2$)—Cys]$_n$,

[Cys—(R$_2$)—Pen]$_n$,

[His—(R$_2$)—Cys]$_n$,

[His—(R$_2$)—Pen]$_n$,

[His]$_n$ and ([His-(R$_2$)-His]$_n$ wherein, n is a number between 1 and about 6; and $R_2$ is an amino acid sequence containing from 1 to about 20 amino acids. $R_2$ may optionally include all or part of the leukostimulatory domain, or the leukostimulatory domain may be located outside of the metal ion-binding domain.

The peptide composition can optionally further comprise a positively-charged transition metal, wherein complexes comprising the positively-charged transition metal and amino acids selected from the group consisting of sulfur, nitrogen and oxygen-containing amino acids and mixtures thereof, are formed. When the peptide composition is labeled with a medically useful metal ion, the medically useful metal ion displaces the positively-charged transition metal, wherein complexes comprising the medically useful metal ion and metal ion-binding domain comprising amino acids selected from the group consisting of sulfur, nitrogen and oxygen-containing amino acids and mixtures thereof, are formed. The medically useful metal ion-labeled peptide, in an amount effective for imaging, is administered to a patient. The patient's leukocytes, or the subset for which the leukostimulatory domain is specific, are allowed to become immunologically active, and the patient is imaged by metal ion detection means.

The type of metal ion detection imaging used in the method includes gamma scintigraphy, specific photon emission computerized tomography, positron emission tomography and magnetic resonance imaging.

The medically useful metal ion used in the method may be radioactive or paramagnetic, and includes ionic forms of the elements iron, cobalt, nickel, copper, zinc, arsenic, selenium, technetium, ruthenium, palladium, silver, cadmium, indium, antimony, rhenium, osmium, iridium, platinum, gold, mercury, thallium, lead, bismuth, polonium and astatine. The medically useful metal ion may also be a radionuclide comprising a member selected from the group consisting of isotopes of indium, gold, silver, mercury, technetium, rhenium and copper.

The method may be accomplished by parenteral administration of the medically useful metal ion-labeled peptide. Such parenteral administration may be by intradermal, subcutaneous, intramuscular, intraperitoneal or intravenous injection.

Accordingly, it is an object of the present invention to provide one-step labeling for the rapid production of Tc-99m-PHA-L4 for the in vivo tagging and activation of T-cells so that location and movement within the body can be determined as a function of time. This radiopharmaceutical will thus be used to diagnose diseases in which the location and trafficking of T-cells is altered such as occurs in some chronic inflammations.

It is a further object of the present invention to provide a means whereby diseases, including abscesses, inflammation, lesions or tumors, can be diagnosed.

It is a further object of the present invention to provide a quick and reproducible method for the in vivo tagging of T-cells in both humans and in other animals.

Another object of the present invention to provide a method for the combined tagging of T-cells with a radioisotope and to simultaneously cause T-cells to become activated.

Another object of the present invention to provide a method for the combined tagging of T-cells with a paramagnetic metal ion and to simultaneously cause T-cells to become activated.

Another object of the present invention is to provide labeling kits which can be used for radiolabeling with radioisotopes of Tc, Re, Cu, Au, Pb, As, Hg, Ag and other radiometals which are gamma or positron emitters and may be useful for diagnostic imaging.

Other objects, advantages and novel features, and further scope of applicability of the present invention will be set forth in part in the detailed description to follow and in part will become apparent to those skilled in the art upon examination of the following, or may be learned by practice of the invention. The objects and advantages of the invention may be realized and attained by means of the instrumentalities and combinations particularly pointed out in the appended claims.

DETAILED DESCRIPTION OF THE PREFERRED EMBODIMENTS OF THE INVENTION (BEST MODES FOR CARRYING OUT THE INVENTION)

Using the methods of this invention, a leukostimulatory agent which binds to leukocytes may be radiolabeled and used to diagnosis conditions in humans and other mammals involving infections, inflammation, tumors, lesions, and similar conditions, and to study the trafficking of stimulated lymphocytes. One preferable class of leukostimulatory agents is lectins, with the preferable lectin being the plant-derived lectin, phytohemagglutinin, and particularly the L4 isolectin of phytohemagglutinin (PHA-L4), which binds the CD3 receptor on T-lymphocytes. Other isotypes and forms of phytohemagglutinin may be employed, including those comprising an aqueous extract of the beans of the genus *Phaseolus*, especially the red kidney bean, *Phaseolus vulgaris*. In addition, synthetic or genetically engineered constructs may be employed that functionally act like PHA-L4, or other leukostimulatory agents, by binding to a lymphocyte membrane antigen to form a stimulatory complex. The term "PHA-L4" as used throughout the specification and claims is intended to include all of the foregoing. Other lectins and mitogenic substances, derived from plants, animal tissues or micro-organisms, may be employed, provided they are leukostimulatory, including concanavalin A (Con A) and pokeweed mitogen.

The leukostimulatory agent may also be an antibody, including whole antibodies and antibody fragments, of any species, and including both polyclonal and monoclonal antibodies made by any means, as well as chimeric and genetically engineered antibodies, and antibody fragments of all of the foregoing. This includes immunoglobulins of any class, such as IgG, IgM, IgA, IgD or IgE; of any species origin, including human beings; chimeric antibodies or hybrid antibodies with dual or multiple antigen or epitope specificities; fragments of all of the foregoing, including F(ab')$_2$, F(ab)$_2$, Fab', Fab and other fragments, including hybrid fragments; and further includes any immunoglobulin or any natural, synthetic or genetically engineered protein that functionally acts like an antibody by binding to a specific lymphocyte membrane antigen to form a stimulatory complex. The term "antibody" or "antibodies", as used throughout the specification and claims is intended to include all such antibodies and antibody fragments.

The term "leukostimulatory" as used throughout the specification and claims is intended to include substances which cause leukocytes, including lymphocytes (B cells, T cells, T cell subsets and the like), granulocytes, monocytes, and the like, to become immunologically active. Most uses of the invention will involve lymphocytes, and in particular T cell subsets.

The term "patient" is intended to denote a mammalian individual. The primary applications of the invention involve human patients, but the invention may be applied to laboratory, farm, zoo, wildlife, pet or sport animals.

It is also possible to synthesize a peptide which binds to a specific lymphocyte membrane antigen to form a stimulatory complex, and which constitutes a leukostimulatory agent. The peptide can be synthesized from amino acid building blocks, and contain a biological function domain and metal binding domain, with the metal binding domain including at least one cysteine amino acid. Regardless of the peptide used, if it does not contain a metal binding domain including at least one cysteine amino acid, it can be chemically modified by the introduction of disulfide bonds.

A variety of peptide and peptide-related sequences may be employed which are leukostimulatory, or which have leukostimulatory properties. Such peptides and peptide-related sequences may stimulate or activate a broad range of leukocytes, or may be specific to one or more specifically defined leukocytes. Examples of peptide and peptide-related sequences which may be employed in this invention include the "neutrophil-activating peptide 2", or "NAP-2", which is comprised of the following amino acid sequence, employing standard abbreviations:

Ala-Glu-Leu-Arg-Cys-Met-Cys-Ile-Lys-Thr-Thr-Ser-Gly-Ile-His-Pro-Lys-Asn-Ile-Gln (SEQ. ID NO. 1)

Walz, A. and Baggiolini, M., "A novel cleavage product of β-thromboglobulin formed in cultures of stimulated mononuclear cells activates human neutrophils," *Biochem Biophys Res Commun* 159:969–975, 1989. This peptide, as well as a related cytokine called "gro/melanoma growth stimulatory activity", have been demonstrated to interact with a human neutrophil receptor for interleukin 8 (IL-8), and to recruit and activates neutrophil leukocytes. Moser, B. et al., "Neutrophil-activating peptide 2 and gro/melanoma growth stimulatory activity interact with neutrophil-activating peptide 1/interleukin 8 receptors on human neutrophils," *J Biol Chem* 266:10666–10671, 1991; and, Schumacher, C., et al., "High- and low-affinity binding of GRO a and neutrophil-activating peptide 2 to interleukin 8 receptors on human neutrophils," *Proc Natl Acad Sci USA* 89:10542–10546, 1992. All such peptides, including related cytokines, such as IL-8, may be employed in this invention.

Other peptides having immunostimulating properties, and which bind human leukocytes, have been identified. Jaziri, M., et al., "Specific binding sites on human phagocytic blood cells for Gly-Leu-Phe (SEQ ID No. 2) and Val-Glu-Pro-Ile-Pro-Tyr, (SEQ ID No. 3) immunostimulating peptides from human milk proteins," *Biochim Biophys Acta* 1160:251–261, 1992. Thus, the tripeptide Gly-Leu-Phe (SEQ ID No. 2) binds to and activates polymorphonuclear leukocytes and monocytes, while the hexapeptide Val-Glu-Pro-Ile-Pro-Tyr (SEQ ID No. 3) binds to and activates only monocytes.

Other agonists of leukocytes, and particularly neutrophils, are known. For example, the compound MePhe-Lys-Pro-D-Cha-Phe-D-Arg is known to be an agonist for most polymorphonuclear leukocyte assays, although it does behave as an antagonist on the release of superoxide by neutrophils. Drapeau, G., et al., "Synthetic C5a receptor agonists: pharmacology, metabolism and in vivo cardiovascular and hematologic effects," *Biochem Pharma* 45:1289–1299, 1993.

In Rhodes B A, U.S. Pat. No. 5,078,985, Radiolabeling Antibodies and Other Proteins with Technetium or Rhenium by Regulated Reduction, a process is taught in which disulfide bonds are first partially reduced with stannous salts or other disulfide reducing agents, the resulting combination is purified, and a specified amount of radionuclide reducing agent is added.

In Rhodes, B. A., U.S. Pat. No. 5,102,990, entitled Direct Radiolabeling of Antibodies and Other Proteins with Technetium or Rhenium, a method, product and kit is provided, wherein proteins containing one or more disulfide bonds are radiolabeled with radionuclides for use in diagnosis and treatment of a variety of pathologic conditions. Radiolabeling is accomplished by partial reduction of the disulfide bonds of the protein using Sn (II), or using other reducing agents followed by the addition of Sn (II), removal of excess reducing agent and reduction by-products, and addition of a specified amount of radionuclide reducing agent, such as stannous tartrate, with the addition accomplished in such a manner that further reduction of the protein is limited. The methods and kit of the '275 application are useful in the present invention. The discussions therein pertaining to technetium and rhenium are also appropriate for the other radiometals and metal ionic forms described herein. Accordingly, the teachings of this application are incorporated herein by reference.

In Rhodes, B. A. and Zamora, P. O., U.S. Pat. No. 5,460,785, entitled Direct Labeling of Antibodies and Other Proteins with Metal Ions, a method is taught in which a protein substrate containing monosulfides or disulfide bonds is labeled with a medically useful metal ion by the following method:

a) incubating the protein with a reducing agent to reduce some or all of the disulfide bonds to thiolate groups, or to maintain monosulfides as thiolate groups;

b) removing excess reducing agent from the protein substrate containing thiolate groups;

c) adding a source of Sn (II) agent to the thiolate-containing protein preparation in an amount sufficient to form Sn (II)-containing and sulfur-containing complexes; and, d) adding a medically useful metal ion whereby the metal ion displaces the Sn (II) in the Sn (II)-containing and sulfur-containing complexes and the metal ion and thiolate-containing protein form metal ion-containing and sulfur-containing complexes.

It is possible to chemically modify the protein by the introduction of disulfide bonds. A protein, even though it may not natively contain monosulfides or disulfide bonds, can be labeled with attached or complexed disulfide bonds. The medically useful metal ions includes ionic forms of the elements iron, cobalt, nickel, copper, zinc, arsenic, selenium, technetium, ruthenium, palladium, silver, cadmium, indium, antimony, iodine, rhenium, osmium, iridium, platinum, gold, mercury, thallium, lead, bismuth, polonium and astatine. Some medically useful metal ions are radioactive, such as radionuclidic isotopes of indium, gold, silver, mercury, technetium, rhenium and copper. The medically useful metal ion can also be paramagnetic. The product resulting from the application of this method can be used for gamma scintigraphy, specific photon emission computerized tomography, magnetic resonance imaging, positron emission tomography and radiotherapy. The discussions therein pertaining to medically useful metal ions are also appropriate for use with the leukostimulatory agents for leukocyte tagging described herein. Accordingly, the teachings of this application are incorporated herein by reference.

In Rhodes, B. A., U.S. Pat. No. 5,346,687, entitled Direct Radiolabeling of Antibody Against Stage Specific Embryonic Antigen for Diagnostic Imaging, antibody against stage specific embryonic antigen-1 is radiolabeled by direct means with a radionuclide for use in detection of occult abscess and inflammation. Radiolabeling is accomplished by partial reduction of the disulfide bonds of the antibody using Sn(II), or using other reducing agents followed by the addition of Sn(II), removal of excess reducing agent and reduction by-products, and addition of a specified amount of radionuclide reducing agent, such as stannous tartrate. The antibody is specific for human granulocytes, and can be used to image sites of occult abscess and inflammation. This antibody is, however, not leukostimulatory. The discussions therein are also appropriate for use with the leukostimulatory agents for leukocyte tagging described herein. Accordingly, the teachings of this application are incorporated herein by reference.

In Zamora, P.O. and Rhodes, B. A., U.S. Pat. No. 5,443,816, entitled Peptide-Metal Ion Pharmaceutical Preparation and Method, peptides containing a biological-function domain and a medically useful metal ion-binding domain are labeled with medically useful metal ions for use in diagnosis and treatment of a variety of pathologic conditions. The peptides have the amino acid sequence ($R_1$)—[Cys]$_n$—($R_2$), ($R_1$)—[Cys—($R_2$)—Cys]$_n$—($R_3$), ($R_1$)—[Cys—($R_2$)—Pen]$_n$—($R_3$), ($R_1$)—[His—($R_2$)—Cys]$_n$—($R_3$), ($R_1$)—[His—($R_2$)—Pen]$_n$—($R_3$), or ($R_1$)—[His—($R_2$)—His]$_n$—($R_3$)

wherein [ . . . ]$_n$ is the medically useful metal ion-binding domain and n is a number between 1 and about 6, wherein the biological function domain is selected from at least one of the group consisting of $R_1$, $R_2$ and $R_3$, and wherein $R_1$, $R_2$ and $R_3$ each comprise an amino acid sequence containing from 0 to about 20 amino acids. The metal ion-binding domain of the peptide is a sequence of one or more amino acids containing sulfur, nitrogen or oxygen which is available for binding or can be made available for binding to metal ions. Sulfur-containing amino acids include primarily cysteine (Cys), cystine (Cys-Cys) and penicillamine (Pen), although deacylated methionine (Met) may also be used. Nitrogen-containing amino acids include primarily histidine (His), but under certain conditions lysine (Lys) and arginine (Arg), which have $pK_a$ values of 10.0 and 12.0, may also be employed. In addition, the terminal amino group of peptides may also be employed. Oxygen-containing amino acids include aspartic acid (Asp), glutamic acid (Glu) and tyrosine (Tyr), as well as the terminal carboxyl group of peptides. The amino acid sequences most usefully employed will include one or more Cys, one or more His, or a combination of Cys and His. Pen, which is an analogue of Cys, may be directly substituted for any given Cys. Cys may be present in the peptide as a disulfide in the form of cystine. The metal ion-binding domains may occur once or multiple times in any given peptide, and may occur in any combination. The metal ion-binding domain and the biological function-domain may overlap. The resulting product may be stored frozen or lyophilized, with labeling accomplished by the addition of the medically useful metal ions. The medically useful metal ion may be radioactive or paramagnetic, with diagnosis performed by gamma scintigraphy, specific photon emission computerized tomography, positron emission tomography or magnetic resonance imaging. The discussions therein are also appropriate for use with the leukostimulatory agents for leukocyte tagging described herein, and specifically, with peptides or peptide sequences which are leukostimulatory. Accordingly, the teachings of this application are incorporated herein by reference.

Because of the earlier, clinical and laboratory studies of PHA, its toxicity is known. The amounts needed for tracer studies, about 10–100 micrograms per 60 kilogram subject, are far below the toxic levels. The $LD_{50}$ for intravenously administered, native PHA in mice is 4–8 mg per kilogram (Weber, T., "Kinetics of the reaction of kidney-bean leuko-agglutinin with human lymphocytes," *Experientia* 29:863–865, 1973), giving an estimated safety factor of more than 2000. In addition, at least part of the observed toxicity is due to the erythroagglutinating characteristic of native PHA, which is absent in the preferred form of PHA-L4 isolectin. Like monoclonal antibodies, PHA can act as an antigen, which occasionally could limit repeat studies in the same subject. Astoldi, G., Airo, R., Lisino, T., et al, "Antibodies to phytohaemagglutinin," *Lancet* 2:502–503, 1966; and, Byrd, W. J., Harek, K., Finley, W. H., et al, "Inhibition of the mitogenic factor in phytohaemagglutinin by an antiserum," *Nature* 213:622–624, 1967.

It is hypothesized that stimulated lymphocytes traffic differently than do unstimulated lymphocytes. One of the differences appears to be that the ratio of stimulated lymphocytes to unstimulated lymphocytes is greater in lesions than in normal tissue. Lymphocytes that are simultaneously radiolabeled and stimulated with radiometal-PHA-L4 will accumulate in both inflammatory lesions and in tumors in greater numbers and ratios than will unstimulated lymphocytes. Because the tagging of the cells will occur in vivo, labeling the lymphocytes will be much simpler than with the most common prior art method, which requires isolating the lymphocyte fraction from a patient's own blood, labeling the cells with $^{111}$In oxine, and then reinjecting the labeled cells into the patient. The labeled cells will suffer less radiation damage than occurs as a result of labeling with $^{111}$In.

Other lectins have leukostimulatory properties, and may be used. These lectins include Concanavalin A (Con A) and pokeweed mitogen. Greaves, M. F., Bauminger, S., Janossy, G., "Lymphocyte activation. III. Binding sites for phytomitogens on lymphocyte subpopulations," *Clin Exp Immunol* 10:537–554, 1972. In addition to lectins, there are antibodies and other related substances which have leukostimulatory properties. Seaman, W. E. and Wofsy, D., "Selective manipulation of the immune response in vivo by monoclonal antibodies," *Ann Rev Med* 39:231–241, 1988. One such antibody is OKT-3, which binds to the CD3 receptor on human T-cells.

Certain lectins may be employed which are specific for certain subsets of leukocytes, such as lectins which are specific for polymorphonuclear leukocytes. For example, a lectin from *Lotus tetragonolobus* both binds to and results in a chemotactic response by normal human polymorphonuclear leukocytes. VanEpps, D. E. and Tung, K. S. K., "Fucose-binding *Lotus tetragonolobus* lectin binds to human polymorphonuclear leukocytes and induces a chemotactic response," *J Immun* 119:1187–1189, 1977. Besides plant-derived lectins, there are a broad range of lectins associated with the surface of bacteria and other cells; such lectins can distinguish not only between different monosaccharides, but also between different oligosaccharides. Bacteria with surface lectins have been shown to specifically bind to leukocytes, including particularly lymphocytes. Such lectins could also be employed in this invention. Sharon, N. and Lis, H., "Carbohydrates in cell recognition," *Sci American* January 1993, pp. 82–89.

In the preferred embodiment, diaminedithiol conjugated PHA-L4 is treated with stannous glucoheptonate such that there is approximately 50 µgm of added tin in the form of Sn(II) per mg of the PHA-L4 conjugate. Lyoprotectants are added and the resulting mixture vialed so that 100 µgm of PHA-L4 is placed in each vial, the vials lyophilized and then backfilled with nitrogen gas and sealed. To prepare the radiopharmaceutical, up to 50 mCi of sodium pertechnetate in saline is added, causing the diaminedithiol conjugated PHA-L4 to come into solution, the pertechnetate to be reduced and the reduced technetium bound to the PHA-L4 by transchelation from the glucoheptonate. The Tc-99m-PHA-L 4 can then be injected into patients for use with a gamma ray imaging device to determine the concentration and movement of T-cells within the body.

In another embodiment, a leukostimulatory proteinaceous substrate, which may be a peptide or polypeptide, containing monosulfides or disulfide bonds is labeled with a medically useful metal ion by the following method:

a) incubating the protein with a reducing agent to reduce some or all of the disulfide bonds to thiolate groups, or to maintain monosulfides as thiolate groups;

b) removing excess reducing agent from the protein substrate containing thiolate groups;

c) adding a source of Sn (II) agent to the thiolate-containing protein preparation in an amount sufficient to form Sn (II)-containing and sulfur-containing complexes; and, d) adding a medically useful metal ion whereby the metal ion displaces the Sn (II) in the Sn (II)-containing and sulfur-containing complexes and the metal ion and thiolate-containing protein form metal ion-containing and sulfur-containing complexes.

The order of the steps may be altered, and the method will still produce metal ion-labeled proteins; the steps in the specification and claims are not limited to the order of steps presented. Specifically, it is possible, and in some cases advantageous, to add the Sn (II) to form Sn (II)-containing and sulfur-containing complexes prior to removing excess reducing agent from the protein substrate. In this way, oxidation of thiolate groups or reformation of disulfide bonds and other cross-linkages is immediately prevented.

Any leukostimulatory protein, peptide, oliopeptide, glycopeptide, glycoprotein, amino acid sequence, or other substrate which contains one or more disulfide bonds or one or more monosulfides, including fragments of any of the foregoing or molecules formed by attaching or complexing any of the foregoing to another molecule, can be labeled as set forth above.

Some proteinaceous substances, such as phytohemagglutinin and the L-4 isolectin thereof, do not natively contain disulfide bonds. It is also possible to chemically modify the substance by the introduction of disulfide bonds. A proteinaceous substance, even though it may not natively contain monosulfides or disulfide bonds, with attached or complexed disulfide bonds can be labeled in accordance with this invention. Means to attach or complex disulfide bonds, and chelating agents and substrates containing disulfide bonds, are known to those skilled in the art. Disulfide bonds may be introduced into such proteins by chemical methods involving direct conjugation. Chemical means used to introduce disulfide bonds into proteins include use of homofunctional crosslinkers, heterofunctional crosslinkers, and monofunctional protein modification agents. Representative chemicals which can be used to introduce disulfide bonds into proteins include 4-succinimidyloxycarbonyl-alpha-methyl-alpha-(2-pyridyldithiol)toluene; N-succinimidyl 3-(2-pyridyldithio) propionate; sulfosuccinimidyl 6-[3-(2-pyridiyldithiol) propinoamido] hexonate; dithiobis (succinimidylproprionate); 3,3'-dithiobis (sulfosuccinimidylpropionate); and sulfosuccinimidyl 2-(p-azidosalicylamido)-ethyl-1,3'-dithiopropionate.

The proteinaceous substrate of this invention is reacted with a medically useful metal ion. The medically useful metal ion may be radioactive and generate gamma rays, beta particles, or positrons which are converted into gamma rays upon collision with electrons. Alternatively, the medically useful metal ion may be paramagnetic. The medically useful metal ion may used in diagnostic imaging procedures including gamma scintigraphy, specific photon emission computerized tomography, or positron emission tomography. The medically useful metal ion may also be used in magnetic resonance imaging.

The type of medically useful metal ion depends on the specific medical diagnostic application. Particularly attractive metal ions can be found in the group consisting of elements 26–30 (Fe, Co, Ni, Cu, Zn), 33–34 (As, Se), 42–50 (Mo, Tc, Ru, Rh, Pd, Ag, Cd, In, Sn), 53 (I) and 75–85 (Re, Os, Ir, Pt, Au, Hg, T1, Pb, Bi, Po, At). The isotope $^{99m}$Tc is particularly applicable for use in diagnostic imaging.

For those proteinaceous substances which natively have disulfide bonds, or to which a disulfide bond has been attached, incubation of the protein with a reducing agent causes reduction of some or all of the disulfide bonds to thiolate groups, and in the case of proteins with monosulfides, causes the monosulfides to be maintained as thiolate groups. Numerous reducing agents have been described and are known to those skilled in the art. Particularly attractive types of reducing agents include 2-mercaptoethanol; 1,4 dithiotheitol; 2,3 dihyroxylbutane-1,4-dithiol; 2-aminoethanethiol HCl; 2-mercaptoethylamine; thioglycolate; cyanide; cysteine; reduced glutathione; Sn (II); Cu (I); and Ti (II). The reducing agent may be dissolved in a solute or may be attached to a solid phase. Reducing agents attached to a solid phase are commercially available, and methods for their use are known to those skilled in the art. The degree to which the protein requires disulfide bond reduction depends on the nature of the protein and its intended medical application. In any event, reduction is halted before excessive fragmentation of the protein or loss of the biological function of the protein occurs.

In one specific embodiment, Sn (II) is used as a reducing agent at a concentration of 5 mM. In this embodiment the Sn (II) is dissolved in a buffer composed of 10 mM tartrate and 40 mM phthalate, pH 5.5, and the Sn (II) buffer admixed with a protein substrate at a concentration of 8.3 mg/ml. The reduction reaction is allowed to proceed for 21 hours at room temperature, after which time the reaction is terminated by removing excess Sn (II) ions by molecular sieve chromatography. One means of molecular sieve chromatography employs Sephadex G-25, with the chromatography gel pre-equilibrated, and the protein eluted in 0.9% NaCl or other suitable buffer.

Removal of the reducing agent, whether Sn (II) or some other reducing agent, can be accomplished by a variety of suitable means, including such methods as dialysis, ultrafiltration, positive-pressure membrane filtration, precipitation, preparative high performance liquid chromatography, affinity chromatography, other forms of chromatography and preparative isoelectric focusing. Many of the reducing agents contain thiols, which if present in the final labeling mixture, can complex with the medically useful metal ion. Such complexes can have severe and unknown side effects if administered in vivo. Additionally, some reducing agents exhibit unacceptable toxicity. Thus removal of the reducing agent both limits the degree of reduction to that desired, as well as providing for increased utility and safety of the labeled preparation by removal of toxic or otherwise undesirable reducing agents.

Thiolate groups in reduced proteins are highly reactive and can interact to form disulfide bonds. The use of Sn (II) is believed to minimize the reformation of disulfide bonds. Sources of Sn (II) include stannous tartrate, stannous glucoheptonate, stannous gluconate, stannous phosphonate, stannous chloride, and stannous fluoride. The selection of the source of Sn (II) and its final concentration depends on the intended medical application of the protein, the nature of the protein, the relative and absolute number of thiolate groups and the metal ion to be used. In one embodiment stannous tartrate is used at a concentration of 1.25 mM. The stannous tartrate is added to the protein after removal of the protein-reducing agent. The stannous tartrate is prepared in a buffer composed of 10 mM tartrate and 40 mM phthalate, pH 5.6, and is added to protein to yield a final concentration of 1 mg/ml protein solution.

Sn (II) can be stabilized by use of dicarboxylic acids, such as phthalate and tartrate. A wide range of dicarboxylic acids, known to those skilled in the art, may be similarly used to stabilize the Sn (II) and/or to act as a buffer. If the phthalate and tartrate are in molar excess relative to the Sn (II), then these dicarboxylic acids also stabilize the medically useful metal ion in a form which can react with the protein. In one embodiment tartrate and phthalate are used in the Sn (II) agent at concentrations of 10 mM and 40 mM, respectively.

Similarly, the Sn (II) and the medically useful metal ion may be stabilized by amino acids used singly or in combination with other agents. The type of amino acid used and the specific concentration depends on the nature of the protein and its intended use. In one embodiment, glycine is used at a concentration of 0.1–10 mM, and in another, histidine is used at a concentration of 0.1–10 mM.

The protein may be stored frozen in bulk form after disulfide bond reduction and the removal of excess reducing agent. Alternatively, the protein may be stored in bulk form or in unit dose form after addition of the Sn (II). Similarly, the protein may be stored lyophilized during or after processing. For example, in one embodiment the protein is stored in vials after introduction of the Sn (II). Methods used in lyophilization of proteins are known to those skilled in the art. Either frozen or lyophilized preparations may be maintained for an indefinite period before labeling by the addition of the medically useful metal ion.

In both the frozen and lyophilized storage forms, excipients may be added to the protein to minimize damage which can arise from ice-crystal formation or free-radical formation. The type of excipient and the concentration depends on the nature of the protein and the intended use. In one embodiment, glycine and inositol are used as excipients in lyophilized preparations.

A typical lyophilized preparation made by the embodiments set forth above would, upon rehydration, contain 10 mM tartrate, 40 mM phthalate, 22 μg of Sn (II), 500 μg of protein, 2 mg/ml of glycine, and 2 mg/ml of inositol. The amounts of protein and Sn (II) used in the kits would depend on the medical application, varying depending on biodistribution of the protein, imaging modality being used, type of metal ion and related factors. Similarly, the amount and type of buffer components (such as tartrate and phthalate) and excipients (such as glycine and inositol) depends on the specific application.

To label with a medically useful metal ion, a typical lyophilized preparation is hydrated by the addition of a solution containing 0.9% NaCl (U.S.P.) or water for injection (U.S.P.) and the medically useful metal ion. Alternatively, it is possible to hydrate the lyophilized preparation, and to add the metal ion in a subsequent step. If a frozen preparation is used, it is thawed and allowed to come to room temperature, and a solution containing the medically useful metal ion is then added. The nature and amount of the medically useful metal ion and the specific reaction conditions depend on the isotopic nature of the metal, and the intended medical application. In one embodiment, $^{99m}$Tc is added in the form of pertechnetate ion in a solution of 0.9% NaCl. The $^{99m}$Tc is typically incubated for up to 30 minutes to insure completion of the reaction with the protein, after which the radiolabeled preparation can be directly used in medical applications. In another embodiment, $^{67}$Cu is added in a solution of 10 mM tartrate and 40 mM phthalate at pH 5.6. In yet another embodiment, $^{188}$Re or $^{186}$Re is added to a solution of 10 mM tartrate and 40 mM phthalate, at pH 5.6, and containing Sn (II), and then heated to lower the oxidation state of Re. The resulting solution is then added to the lyophilized or frozen preparation.

In the embodiment in which $^{99m}$Tc is used, the Sn (II) is present in the protein-containing solution in sufficient excess to alter the oxidation state of the Tc ion such that it can bind to thiolate groups. Typically Tc (VII) is reduced to Tc (III), Tc (VI), and/or Tc (V). The preferred state of Tc to be added to protein preparations is as the pertechnetate ion, (TcO$_4$). The Sn (II) then reacts with the pertechnetate ion resulting in a composition in which the Tc is in a lower oxidation state and is reactive with thiolate groups. Similar approaches may be used to lower the oxidation state of other medically useful metal ions for subsequent binding to thiolate groups. The type of the metal ion, its isotopic nature, and concentration would depend on the intended medical application.

The product resulting from the methods set forth herein can be used for both medical applications and veterinary applications. Typically, the product is used in humans, but may also be used in other mammals. The product may be used to monitor normal or abnormal metabolic events, to localize normal or abnormal tissues, to localize diseases, and to bind to blood constituents, including blood cells, such as lymphocytes, for subsequent localization of diseases, infections, and abnormal tissues. The application and medical use of the product depends on the type of protein and the type of medically useful metal ion used.

The product can be used in a variety of medical procedures including gamma scintigraphy, specific photon emission computerized tomography, positron emission tomography, and magnetic resonance imaging. The medical application of the product of this invention depends on the type of protein and the type of medically useful metal ion used.

The invention is further illustrated by the following non-limiting examples.

EXAMPLE I

The PHA-L4 isolectin was obtained from E-Y Laboratories (San Mateo, Calif.), and was determined to have a purity of 97%, as determined by HPLC. PHA-L4 was radiolabeled with $^{125}$I, and binding of the radiolabeled material to lymphocyte-membrane proteins attached to a solid phase was demonstrated. Radioiodination was accomplished using the Iodobead method, following the manufacturer's instructions (Pierce Chemical, Rockford, Ill.). Table 1 contains data showing binding of PHA-L4 preparations to the solid phase membrane proteins and the lack of binding of a control material, casein.

Binding of the radiolabeled isolectin was determined by measuring the percentage of the total radioactivity that bound to the solid-phase binding protein, as described by Rhodes, et al. Rhodes, B. A., Buckelew, J. M., Pant, K. D., et al, "Quality control test for immunoreactivity of radiolabeled antibody," *BioTechniques* 8:70–74, 1990. Solid-phase human white blood cells were prepared by separating white blood cells and fixing them to Kynar beads. Human plasma and casein were similarly fixed to Kynar beads. Briefly, $^{125}$I-labeled PHA-L4 was introduced to aliquots of solid-phase antigen, and the initial counts per minute measured. The preparation was allowed to incubate, following which it was washed repeatedly to remove unbound $^{125}$I-labeled PHA-L4, and the final counts per minute were then measured.

TABLE 1

| SPECIFIC BINDING OF $^{125}$I-LABELED PHA-L4 TO SOLID PHASE ANTIGEN | | | |
|---|---|---|---|
| Solid Phase Antigen | Initial CPM | Final CPM | % Bound |
| Human White Blood Cells | 58,469 | 15,983 | 27.4% |
| Human Plasma | 45,707 | 4,914 | 10.8% |
| Casein Control | 46,836 | 1,408 | 3.0% |

EXAMPLE II

PHA-L4 is labeled using the radionuclide $^{99m}$Tc. PHA-L4 is obtained as in Example I. The L4 isolectin will not bind $^{99m}$Tc directly due to the lack of native cysteine in the glycoprotein molecule. However, the PHA-L4 glycoprotein does have an ample number of lysine-containing amino acid groups, which are required for attaching many bifunctional chelate groups. The method used is conjugation of diaminedithiol to the PHA-L4 molecule, as is described by Lever et al. Lever, S. Z., Baidoo, K. E., Kramer, A. V., Burns, H. D., "Synthesis of a novel bifunctional chelate designed for labeling proteins with technetium-99m," *Tetrahedron Lett* 29:3219–3222, 1988. The conjugated PHA-L4 is then labeled with $^{99m}$Tc, using the method described by Baidoo, et al. Baidoo, K. E., Scheffel, U., Lever, S. Z., "$^{99m}$TC labeling of proteins: Initial evaluation of a novel diaminedithiol bifunctional chelating agent," *Cancer Res (Supp)* 50:799s–803s, 1990.

EXAMPLE III

PHA-L4 is labeled by any means known in the art, including labeled with $^{99m}$Tc by the method in Example II. BALB/c mice, male or female, weighing between 18–25 grams, are injected in the right thigh, either with 40 µl turpentine or with 100 µl tissue culture medium containing approximately $5\times10^8$ *E. coli* (ATC-25922) and $5\times10^8$ Enterococci (ATC-29212). The organisms are grown and their numbers estimated by McFarlen assay in the microbiology laboratory. Forty-eight hours after receiving the injection, a gross swelling, approximately 0.5 cm in diameter, appears in the thigh.

Either $^{111}$In oxine-labeled cells or $^{99m}$Tc-PHA-L4-labeled cells are prepared by harvesting blood from the heart of 10 anesthetized mice. The lymphocytes are separated, labeled, and resuspended in the mouse plasma. When labeling with $^{111}$In oxine, standard procedures are used. To label the lymphocytes with either PHA-L4 or $^{99m}$Tc-PHA-L4, the isolectin is added to the lymphocyte/plasma suspension and allowed to incubate for 1 hour at 37° C. PHA binds rapidly to lymphocytes, and this binding appears to be non-reversible after a 1-hour incubation. Lindahl-Kiessling, K. L., "Mechanism of phytohemagglutinin (PHA) action. V. PHA compared with concanavalin A (Con A)," *Exp Cell Res* 70:17–26, 1972. The cells are then centrifuged, the supernatant removed, and the cells resuspended in plasma. At an initial dosage of 10 µg of isolectin per $10^7$ cells per ml of plasma, the cells are labeled by high affinity bonding that apparently connects the PHA to two CD3 receptors and thus, avoids crosslinking the PHA between two T-cells, which can lead to leukoagglutination.

The labeled cells are administered through the tail vein to groups of five mice, in which inflammation had been induced 48 hours earlier. Approximately 50 µCi of each radionuclide is injected into each animal. The radioactivity in each syringe is measured in a Capintech CRC-10 dose calibrator before and after injection, and recorded. At 4 or 24 hours post injection, the animals are sacrificed by placing them in an airtight jar containing absorbent paper saturated with halothane. The animals are imaged with a gamma camera equipped with a pinhole, collimator, and a Microdot imager. Tissue can also be dissected and weighed, and the concomitant radioactivity counted with an energy-calibrated, gamma counter. Appropriate standards prepared at the time of injection will allow determination of the total cpm received by each animal for each of the two isotopes. Corrections for decay and cross-talk can be made, and the result expressed as a percentage of administered dose per gram of tissue.

EXAMPLE IV

PHA-L4 is labeled by any means known in the art, including labeled with $^{99m}$Tc by the method in Example II. It is then used as a diagnostic radiopharmaceutical for imaging of chronic infections such as osteomyelitis and granulomatous diseases.

EXAMPLE V

Cyclic anhydride of diethylenetriaminepentaacetic acid (DTPA) (Sigma) is coupled to PHA-L4. Sodium pertechnetate is added to a reducing agent, such as stannous chloride or dithionite, and allowed to incubate for ten minutes under nitrogen atmosphere. The reduced $^{99m}$Tc solution is then added to DTPA coupled PHA-L4. Following an incubation, the PHA-L4 can be separated from unbound $^{99m}$Tc, and the percentage of radioactivity associated with the PHA-L4 determined. Similar results can be obtained using $^{111}$In as the radionuclide.

The preceding examples can be repeated with similar success by substituting the generically or specifically described reactants and/or operating conditions of this invention for those in the preceding example. In particular, the leukostimulatory agent employed may be varied, and may include lectins other than PHA-L4, and may further include leukostimulatory antibodies; the methods of radiolabeling PHA-L4 may be varied; the methods of production and purification of PHA-L4 may be varied; different preparations equivalent to PHA-L4 may be used, including genetically engineered materials, and the method of application and imaging may be varied. The foregoing are merely illustrative, and other equivalent embodiments are possible and contemplated.

Although the invention has been described with reference to these preferred embodiments, other embodiments can achieve the same results. Variations and modifications of the present invention will be obvious to those skilled in the art and it is intended to cover in the appended claims all such modifications and equivalents. The entire disclosures of all applications, patents, and publications cited above, and of the corresponding application, are hereby incorporated by reference.

What is claimed is:

1. A method of detecting concentrations of leukocytes in a patient, comprising the steps of:

a) administering to the patient an effective amount of a reagent comprising a leukostimulatory agent, said leukostimulatory agent selected from the group consisting of lectins and peptides, and a linked medically useful imaging ion, under conditions which allow the reagent to bind to leukocytes;

b) allowing the leukocytes to become immunologically active; and c) detecting concentrations of leukocytes by medically useful imaging ion agent detection means.

2. The method of claim 1 wherein said leukocytes are lymphocytes.

3. The method of claim 2 wherein said lymphocytes are T lymphocytes.

4. The method of claim 1 wherein said leukostimulatory agent binds to a CD3 receptor of T lymphocytes.

5. The method of claim 1 wherein said medically useful imaging ion detection means comprises imaging with at least one method selected from the group consisting of gamma scintigraphy, specific photon emission computerized tomography, positron emission tomography and magnetic resonance imaging.

6. The method of claim 1 wherein said medically useful imaging ion comprises at least one member selected from the group consisting of indium, technetium, gallium, ruthenium, iodine, yttrium, lead and copper.

7. The method of claim 1 wherein said medically useful imaging ion is linked to the lectin via a chelating agent.

8. A method of detecting concentrations of leukocytes in a patient, comprising the steps:

a) preparing a reagent comprising a peptide comprising a leukostimulatory domain and a metal ion-binding domain selected from the group consisting of $(R_1)$—$[Y_1]_n$—$(R_2)$,
   $(R_1)$—$[Y_1$—$(R_2)$—$Y_1]_n$—$(R_3)$
   and $(R_1)$—$[Y_1$—$(R_2)$—$Y_2]_n$—$(R_3)$ wherein, the medically useful metal ion-binding domain is selected from one of the group consisting of $[Y_1]_n$, $[Y_1$-$(R_2)$-$Y_1]_n$ and $[Y_1$-$(R_2)$-$Y_2]_n$ in which n is a number between 1 and about 6 and $Y_1$ and $Y_2$ comprises amino acids which are available for binding to metal ions, or can be made available for binding to metal ions, selected from the group consisting of sulfur, nitrogen and oxygen-containing amino acids and mixtures thereof;

the leukostimulatory domain comprises at least one of the group consisting of $R_1$, $R_2$ and $R_3$ and further comprises an amino acid sequence containing from 1 to about 20 amino acids;

those portions of $R_1$, $R_2$ and $R_3$ not comprising the leukostimulatory domain each comprise an amino acid sequence containing from 0 to about 20 amino acids;

and further comprising a positively-charged transition metal, wherein complexes comprising the positively-charged transition metal and amino acids selected from the group consisting of sulfur, nitrogen and oxygen-containing amino acids and mixtures thereof, are formed;

b) labeling the reagent with the medically useful metal ion, wherein the medically useful metal ion displaces the positively-charged transition metal, wherein complexes comprising the medically useful metal ion and metal ion-binding domain comprising amino acids selected from the group consisting of sulfur, nitrogen and oxygen-containing amino acids and mixtures thereof, are formed;

c) administering to a patient the medically useful metal ion-labeled peptide in an amount effective for imaging;

d) allowing the leukocytes to become immunologically active; and e) imaging by metal ion detection means.

9. The method of claim 8 wherein said medically useful metal ion-binding domain includes an amino acid sequence consisting of at least one amino acid selected from the group consisting of cysteine, penicillamine, deacylated methionine, histidine, lysine, arginine, aspartic acid, glutamic acid and tyrosine.

10. The method of claim 8 wherein the medically useful metal ion-binding domain is selected from the group consisting of $[His$—$R_2$—$Cys]_n$,
   $[His$—$R_2$—$Pen]_n$,
   $[His$ —$R_2$—$His]_n$,
   $[Cys$—$R_2$—$Cys]_n$,
   $[Pen$—$R_2$—$Pen]_n$,
   $[Pen$—$R_2$—$Cys]_n$,
   $[His]_n$,
   $[cys]_n$,
   and $[Pen]_n$, wherein, n is a number between 1 and about 6; and $R_2$ is an amino acid sequence containing from 1 to about 20 amino acids.

11. The method of claim 8 wherein the positively-charged transition metal comprises a stannous ion agent.

12. The method of claim 8 wherein the medically useful metal ion is a radionuclide comprising a member selected from the group consisting of isotopes of indium, gold, silver, mercury, technetium, rhenium and copper.

* * * * *

UNITED STATES PATENT AND TRADEMARK OFFICE
CERTIFICATE OF CORRECTION

PATENT NO.   : 5,643,549
DATED        : July 1, 1997
INVENTOR(S)  : Buck A. RHODES It is certified that error appears in the above-indentified patent and that said Letters Patent is hereby corrected as shown below:

Foremost page, [*], Notice, change "5,227,892" to --5,277,892--.

Signed and Sealed this

Thirtieth Day of December, 1997

Attest:

BRUCE LEHMAN

Attesting Officer

Commissioner of Patents and Trademarks